US006787776B2

United States Patent
Webber et al.

(10) Patent No.: US 6,787,776 B2
(45) Date of Patent: Sep. 7, 2004

(54) GAS SENSOR FOR AMMONIA, CARBON DIOXIDE AND WATER

(75) Inventors: Michael E. Webber, Culver City, CA (US); Ronald K. Hanson, Cupertino, CA (US); Jay B. Jeffries, Palo Alto, CA (US)

(73) Assignee: The Board of Trustees of Leland Stanford Junior University, Stanford, CA (US)

( * ) Notice: Subject to any disclaimer, the term of this patent is extended or adjusted under 35 U.S.C. 154(b) by 78 days.

(21) Appl. No.: 10/219,993

(22) Filed: Aug. 14, 2002

(65) Prior Publication Data

US 2003/0080295 A1 May 1, 2003

Related U.S. Application Data

(60) Provisional application No. 60/313,036, filed on Aug. 16, 2001.

(51) Int. Cl.$^7$ ................................................. G01B 9/02
(52) U.S. Cl. .................................. 250/341.2; 250/341.6
(58) Field of Search ........................... 250/341.2, 341.6, 250/339.08, 339.13, 339.03; 356/311, 315, 484, 312; 600/532, 528, 529; 73/23.3

(56) References Cited

U.S. PATENT DOCUMENTS

| 4,051,372 | A | * | 9/1977 | Aine | ........................... 250/343 |
| 5,473,162 | A | * | 12/1995 | Busch et al. | .............. 250/341.6 |
| 5,957,858 | A | * | 9/1999 | Micheels et al. | ........... 600/529 |
| 6,363,772 | B1 | * | 4/2002 | Berry | ......................... 73/24.02 |
| 6,599,253 | B1 | * | 7/2003 | Baum et al. | ................. 600/532 |
| 2002/0026937 | A1 | * | 3/2002 | Mault | ..................... 128/200.24 |
| 2003/0176804 | A1 | * | 9/2003 | Melker | ........................ 600/532 |
| 2003/0189711 | A1 | * | 10/2003 | Orr et al | .................... 356/484 |

OTHER PUBLICATIONS

Nagali et al., (1996), "Tunable Diode–Laser Absorption Measurements of Methane at Elevated Temperatures," Appl. Opt., 35(21):4026–4032.

Rothman et al, (1998), "The HITRAN Molecular Spectroscopic Database and HAWKS (HITRAN Atmosphere Workstation): 1996 Edition," J. Quant. Spectrosc. Radiat. Transfer, 60:665–710.

Lundsberg–Nielsen et al., (1993), "Analysis of the High–Resolution Spectrum of Ammonia ($^{14}NH_3$) in the near–infrared Region, 6400–6900cm$^{-1}$," J. Mol. Spectrosc., 162:230–245.

(List continued on next page.)

*Primary Examiner*—Constantine Hannaher
*Assistant Examiner*—Otilia Gabor
(74) *Attorney, Agent, or Firm*—Lumen Intellectual Property Services, Inc.

(57) ABSTRACT

A system and method utilizing a radiation source with a wavelength near 2 $\mu$m (preferably 1993 nm) to measure the presence of ammonia, carbon dioxide and water vapor using spectroscopic techniques and a reduced measurement pressure is provided. Using radiation substantially near 2 $\mu$m enables one to interrogate the $^PP_3(3)_s$ ammonia transition at a frequency of 5016.977 cm$^{-1}$, which is isolated from water and carbon dioxide interference; the P(32) carbon dioxide transition at 5017.030 cm$^{-1}$, which is isolated from both ammonia and water interference, and a water transition at 5017.100 cm$^{-1}$. Moreover, a tunable radiation source that can sweep over the aforementioned ammonia and carbon dioxide and water features can measure the concentrations of all three species simultaneously. Using a sub-atmospheric pressure substantially near 100 Torr decreases the pressure broadening of different spectroscopic transitions, thereby isolating different absorption features, enabling species-specific measurements without interference, yet retaining sufficient peak absorption.

55 Claims, 6 Drawing Sheets

OTHER PUBLICATIONS

Lundsberg–Nielsen, (1995), "Molecular Overtone Spectroscopy on Ammonia," Ph.D Dissertation, Department of Chemistry, Univ. of Copenhagen, Danish Institute of Fundamental Metrology, Copenhagen, Denmark.

Mihalcea et al., (1998), Diode Laser Absorption Measurements of $CO_2$, $H_2O$, $N_2O$ and $NH_3$ near 2.0 Micrometer, Appl. Phys., 67:283–288.

Brown et al., (1996), "Empirical Line Parameters of NH3 from 4791 to 5294 cm–1," J. Quant. Spectrosc. Radiat. Transfer, 56(2):283–294.

Sarangi, (1977), "Analysis of the v3×v4 Band of Ammonia," J. Quant. Spectrosc. Radiat. Transfer, 18:257–288.

Sarangi, (1977), "Measurements of Line Intensities in the Two–Micron Band of Ammonia," J. Quant. Spectrosc. Radiat. Transfer 18:289–293.

Webber et al., (2001), "In Situ Combustion Measurements of $CO_2$ by use of a Distributed–Feedback Diode–Laser Sensor near 2.0 $\mu$m," Appl. Opt., 40:821–828.

Webber et al., (2001), "Ammonia Monitoring Near 1.5 mm with Diode Laser Absorption Sensors," Appl. Opt. 40:2031–2042.

Webber et al., (2001),"Measurements of $NH_3$ and $CO_2$ with distributed–feedback diode lasers near 2.0 $\mu$m in bioreactor vent gases," Appl. Opt., 40:4395–4403.

* cited by examiner

GAS SENSOR FOR AMMONIA, CARBON DIOXIDE AND WATER

CROSS-REFERENCE TO RELATED APPLICATIONS

This application is cross-referenced to and claims priority from U.S. Provisional Application No. 60/313,036 filed on Aug. 16, 2001, which is hereby incorporated by reference.

STATEMENT REGARDING FEDERALLY SPONSORED RESEARCH OR DEVELOPMENT

This invention was supported in part by grant number EPA R827123-01-0 from the Environmental Protection Agency. The U.S. Government has certain rights in the invention.

FIELD OF THE INVENTION

The present invention relates generally to systems for measuring gas concentrations of chemical species. More particularly, the present invention relates to systems to measure the presence of trace ammonia gas in the presence of large carbon dioxide and water vapor populations or to measure any combination of ammonia, carbon dioxide and water simultaneously.

BACKGROUND

Most applications for which measurement of trace ammonia concentration is pertinent include high background levels of carbon dioxide and water vapor that can potentially interfere with the measurement. These applications include, but are not limited to, industrial chiller plants, where ammonia leaks that result in a few parts-per-million (ppm) concentration of ammonia in an atmospheric background with approximately 400 ppm carbon dioxide and 2 percent of water need to be detected; car exhaust analysis, for which ppm or less concentrations of ammonia need to be detected in the presence of 5–15% carbon dioxide and 5–20% water vapor; breath analysis, for which sub-ppm concentrations of ammonia need to be detected in the presence of approximately 2–6% carbon dioxide and 5–10% water vapor; and a variety of industrial process systems for which small amounts of ammonia gas need to be detected in the presence of other gases, such as within semiconductor fabrication facilities.

Current systems utilize various different techniques such as, for instance, electrochemical sensors, mass spectroscopy, or chemiluminescence. Many devices, such as electrochemical sensors, are sensitive to interfering species, and thus are not suitable. Mass spectroscopy is a slow, bulky and expensive process. Chemiluminescence, which is sensitive and expensive, actually detects the presence of ammonia via chemical conversion of any species containing nitrogen, and is thus not a direct or absolute measurement. Optical techniques such as laser spectroscopic sensors are advantageous over electrochemical sensors, mass spectroscopy or chemiluminescence because optical techniques could make absolute measurements very quickly, using affordable off-the-shelf components, and without calibration requirements or cross-sensitivity from other species. However, current optical techniques used to measure ammonia are susceptible to interfering absorption of laser radiation by carbon dioxide. This occurs, for example, at many wavelengths near 2 $\mu$m, 1.5 $\mu$m or near 10 $\mu$m. Mihalcea et al. (in a paper entitled *diode laser absorption measurements of $CO_2$, $H_2O$, $N_2O$ and $NH_3$ near 2.0 micrometer* and published in *Appl. Phys.* 67:283:288, 1998) demonstrated that a laser could be used with a wavelength near 2 $\mu$m to measure different species. However, Mihalcea et al. did not teach or anticipate the fundamental parameters, such as the wavelength, transitions or pressure, necessary to measure ammonia substantially free from interference of other species. As a person of average skill in the art would readily appreciate, it would be difficult to determine which parameters work best or are optimal to measure ammonia substantially free from interference of other species. Accordingly, there is a need in the art to develop systems and methods to measure ammonia that are species selective, interference-free, relatively faster than prior art devices and methods, highly-resolved and affordable. Furthermore, there is a need to develop systems and methods that include a careful selection of optimum transitions that offer adequate sensitivity over the range of expected concentration and sufficient isolation from potential interfering species.

SUMMARY OF THE INVENTION

The present invention provides a system and method to measure the concentration of trace ammonia gas in the presence of large background carbon dioxide and water vapor populations. The present invention also provides a system and method to measure any combination of ammonia, carbon dioxide and water simultaneously.

The sensor system and method of the present invention for measuring ammonia in an environment containing carbon dioxide and water vapor include a single radiation source that is capable of spectrally interrogating an ammonia transition in an absorption band at substantially near 2 $\mu$m (preferably 1993 nm). In this measurement the ammonia transition is substantially isolated from interfering absorption from the carbon dioxide and the water vapor. The ammonia transition at a frequency substantially close to 5016.977 inverse centimeters is selected in order to avoid interfering absorption from carbon dioxide and water vapor. For measuring ammonia only, a small scan by the radiation source would suffice.

The radiation source could also spectrally interrogate a carbon dioxide transition in an absorption band at substantially near 2 $\mu$m, whereby the carbon dioxide transition would be substantially isolated from interfering absorption from ammonia and water vapor. The carbon dioxide transition that is used occurs at a frequency substantially close to 5017.030 inverse centimeters in order to avoid interfering absorption from ammonia and water vapor. Furthermore, the radiation source could also spectrally interrogate a water vapor transition in an absorption band at substantially near 2 $\mu$m, whereby the water vapor transition would be substantially isolated from interfering absorption from ammonia and carbon dioxide. The water vapor transition that is used occurs at a frequency substantially close to 5017.100 inverse centimeters in order to avoid interfering absorption from ammonia and carbon dioxide.

The preferred radiation source is an infra-red single-frequency laser. An example of laser systems that could be used in the present invention are for instance, but not limited to, a semiconductor diode laser, a distributed feedback diode laser, a fiber-coupled distributed feedback diode laser, a fiber laser, or an optical parametric oscillator. In order to spectrally resolve the measurements of the different gas species various different techniques could be used. For instance, the system and method of the present invention could utilize scanned- and fixed wavelength absorption, balanced radiometric detection, frequency modulated (FM) spectroscopy, cavity-ring down, stark modulation, evanescent wave, photothermal deflection, optogalvanic spectroscopy or photoacoustic spectroscopy.

The system and method of the present invention further provide a means to operate at sub-atmospheric pressure to yield a good balance between signal strength and isolation of neighboring spectral transitions. The present invention teaches that a sub-atmospheric of substantially near 100 Torr (+/−20 Torr) would be optimal for measurements of ammonia. Using such a sub-atmospheric pressure decreases the pressure broadening of the different spectroscopic transitions, thereby isolating the different absorption features from each other, enabling species-specific measurements without interference from primary bath gas constituents.

As mentioned above, the sensor system and method of the present invention could also be used for measuring different gas species simultaneously with a radiation source (e.g. a tunable laser) that can sweep over the absorption transitions from all species simultaneously. In this case the sensor system and method of the present invention include a single radiation source that operates at a wavelength of substantially near 2 $\mu$m (preferably 1993 nm) for simultaneously measuring a plurality of species along a single optical path in a gas mixture that contains the plurality of species. In this measurement, the absorption transitions that are interrogated for the plurality of species are proximate in frequency such that the radiation source can be scanned or stepped in the wavelength across the absorption transitions of all three species within a single measurement cycle. In the particular embodiment of the present invention, the plurality of species includes at least ammonia, carbon dioxide and water vapor. The present invention is not limited to the use of a single radiation source since it would be possible to include one or more additional radiation sources, for instance in a multiplexed fashion, each operating at a wavelength of substantially near 2 $\mu$m. Each radiation source could interrogate one or more of the transition bands of ammonia, carbon dioxide and/or water vapor. The measurements parameters such as the pressure and temperature conditions are similar for a single and simultaneous measurement.

The present invention could be varied in several ways such as by including optical fibers for remote detection and measurement(s). The present invention could also be varied by providing optical fibers for remote detection or detection of multiple species and/or at multiple locations.

In view of that which is stated above, it is the objective of the present invention to utilize a radiation source to spectrally interrogate an ammonia transition in an absorption band at substantially near 2 $\mu$m, whereby the ammonia transition is substantially isolated from interfering absorption from carbon dioxide and water vapor.

It is still another objective of the present invention to utilize a radiation source to measure $NH_3$ at a frequency of 5016.977 inverse centimeters to avoid $CO_2$ and $H_2O$ interference.

It is still another objective of the present invention to utilize a radiation source to measure $CO_2$ at a frequency of 5017.030 inverse centimeters to avoid $NH_3$ and $H_2O$ interference.

It is still another objective of the present invention to utilize a radiation source to measure $NH_3$ and $CO_2$ simultaneously with a scan that covers both of the aforementioned two objectives.

It is still another objective of the present invention to utilize a radiation source to measure $H_2O$ at a frequency of 5017.100 inverse centimeters to avoid $CO_2$ and $NH_3$ interference.

It is yet another objective of the present invention to measure $NH_3$, $CO_2$ and water vapor simultaneously with a single scan by the radiation source.

It is yet another objective of the present invention to utilize substantially near 100 Torr as the optimum measurement pressure for $NH_3$ measurements to achieve a balance between highest achievable signal and narrowest spectroscopic transition. This optimum pressure is suitable for measurements of $NH_3$ at any wavelength, not just 2 micron.

The present invention overcomes the limitations of prior art devices and methods and is characterized as species selective, interference-free, quick, highly-resolved and affordable. The present invention can be readily applied for in-situ measurements in certain measurement sites, including reduced pressure wafer etch chambers, before wafer damage occurs. The particular isolated ammonia transition at 2 $\mu$m is more sensitive than the best wavelength at 1.5 $\mu$m (where many optical sensors for ammonia operate), and is the strongest in the entire 2 $\mu$m ammonia band that is isolated from both carbon dioxide and water vapor. The present invention takes advantage of lasers that operate near 2 $\mu$m that have become commercially available in the last several years. Another advantage of a sensor that operates near 2 $\mu$m is that standard telecommunications-grade low-OH silica optical fibers can be used in conjunction with the sensor for remote detection, multiplexing, and simultaneous measurement of multiple species and/or at multiple locations. Operating the measurement chamber at reduced pressure achieves better isolation between the target transition and neighboring locations. Though sub-atmospheric pressure is suitable in general, 100 Torr is the optimum pressure for measuring ammonia because that pressure achieves a balance between highest signal and narrowest, i.e. most isolated, transitions. Whereas for other species, for example $CO_2$, 200 Torr is the optimum pressure for achieving highest signal with narrowest transition.

BRIEF DESCRIPTION OF THE FIGURES

The objectives and advantages of the present invention will be understood by reading the following detailed description in conjunction with the drawings, in which.

DETAILED DESCRIPTION OF THE INVENTION

Figure 1:
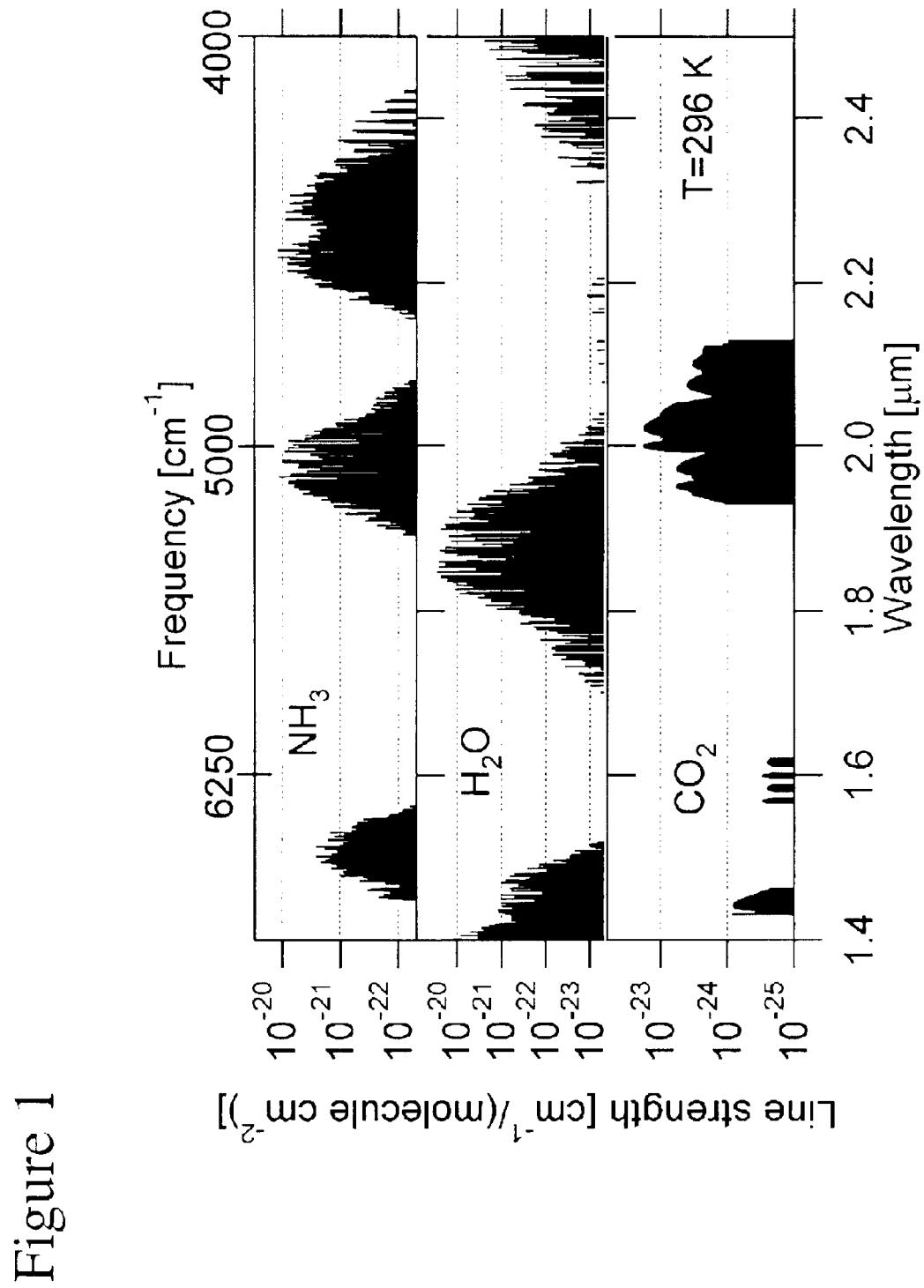
FIG. 1 shows the line-strengths of $NH_3$, $H_2O$ and $CO_2$ in the near-infrared between 1.4 and 2.5 $\mu$m at 296K.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

Theory

The fundamental theory governing absorption spectroscopy for narrow linewidth radiation sources is embodied in the Beer-Lambert law (EQ. 1) and is described thoroughly in the paper by Nagali et al. (1996) entitled "*Tunable diode-laser absorption measurements of methane at elevated temperatures*" and published in Appl. Opt. 35(21):4026–4032, which is hereby incorporated herein by reference. In brief, the ratio of the transmitted intensity $I_t$ and initial (reference) intensity $I_0$ of laser radiation through an absorbing medium at a particular frequency is exponentially related to the transition linestrength $S_i[cm^{-2} atm^{-1}]$, lineshape function $\phi$ [cm], total pressure P [atm], mole fraction of the absorbing species $x_j$, and the pathlength L [cm], such that:

$$\frac{I_t}{I_0} = \exp(-S_i \phi P x_j L). \quad \text{EQ. 1}$$

The normalized line-shape function describes the effects of thermal motion (Doppler broadening) and intermolecular collisions (collisional or pressure Broadening), which have Gaussian and Lorentzian line shapes, respectively. Ammonia and carbon dioxide absorption transitions at room temperature and subatmospheric pressure will have line shapes that are described by the Voigt function, which is a convolution of the Gaussian and Lorentzian functions. Because the line shape is normalized, wavelength tuning the laser across an isolated absorption transition and integrating the area under the line-shape, obviates the need for detailed broadening or line-shape analysis.

The line-strength as a function of temperature for a particular transition i is governed by its line strength $S_t$ at a reference temperature $T_0$, the partition function Q(T) of the absorbing molecule ($CO_2$ or $NH_3$), the frequency of the transition $v_{0,i}$, and the lower-state energy of the transition $E_i''$. This relationship is given by EQ. 2:

$$S_i(T) = S_i(T_0) \frac{Q(T_0)}{Q(T)} \left(\frac{T_0}{T}\right) \exp\left[-\frac{hcE_i''}{k}\left(\frac{1}{T} - \frac{1}{T_0}\right)\right] \times \quad \text{EQ. 2}$$
$$\left[1 - \exp\left(\frac{-hcv_{0,i}}{kT}\right)\right]\left[1 - \exp\left(\frac{-hcv_{0,i}}{kT_0}\right)\right]^{-1}$$

The partition function for $NH_3$ is available in a paper by Webber et al. (2001) entitled "*Ammonia monitoring near 1.5 µm with diode laser absorption sensors*" and published in Appl. Opt. 40:2031–2042. The partition function for $CO_2$ is available in a paper by Rothman et al. (1998) in a paper entitled "*The HITRAN molecular spectroscopic database and HAWKS (HITRAN atmospheric workstation): 1996 edition*" and published in J. Quant. Spectrosc. Radiat. Transfer 60:665–710.

Other absorption-based techniques, such as evanescent wave spectroscopy and photoacoustic spectroscopy, have a similar dependence on the absorption linestrength, and thus the sensitivity of detection systems based on those techniques benefit from the linestrengths near 2 µm that are stronger than those near 1.5 µm.

Line Selection

The design of a laser-based sensor for gas species in an environment with a mixture of gas species requires careful selection of optimum transitions that offer adequate sensitivity over the range of expected populations and isolation from potential interfering species. FIG. 1 shows the line strengths of $NH_3$, $H_2O$, and $CO_2$ in the near infrared between 1.4 and 2.5 µm. (See paper by Rothman et al. (1998) entitled "*The HITRAN molecular spectroscopic database and HAWKS (HITRAN atmospheric workstation)*: 1996 edition" and published in J. Quant. Spectrosc. Radiat. Transfer 60:665–710; a paper by Lundsberg-Nielsen et al. (1993) in a paper entitled "*Analysis of the high-resolution spectrum of ammonia ($^{14}NH_3$) in the near-infrared region, 6400–6900 $cm^{-1}$*" and published in J. Mol. Spectrosc. 162:230–245; and a dissertation by Lundsberg-Nielsen (1995) entitled "*Molecular overtone spectroscopy on ammonia*" Ph.D. dissertation published by the Department of Chemistry, University of Copenhagen, Danish Institute of Fundamental Metrology, Copenhagen, Denmark).

Figure 2:
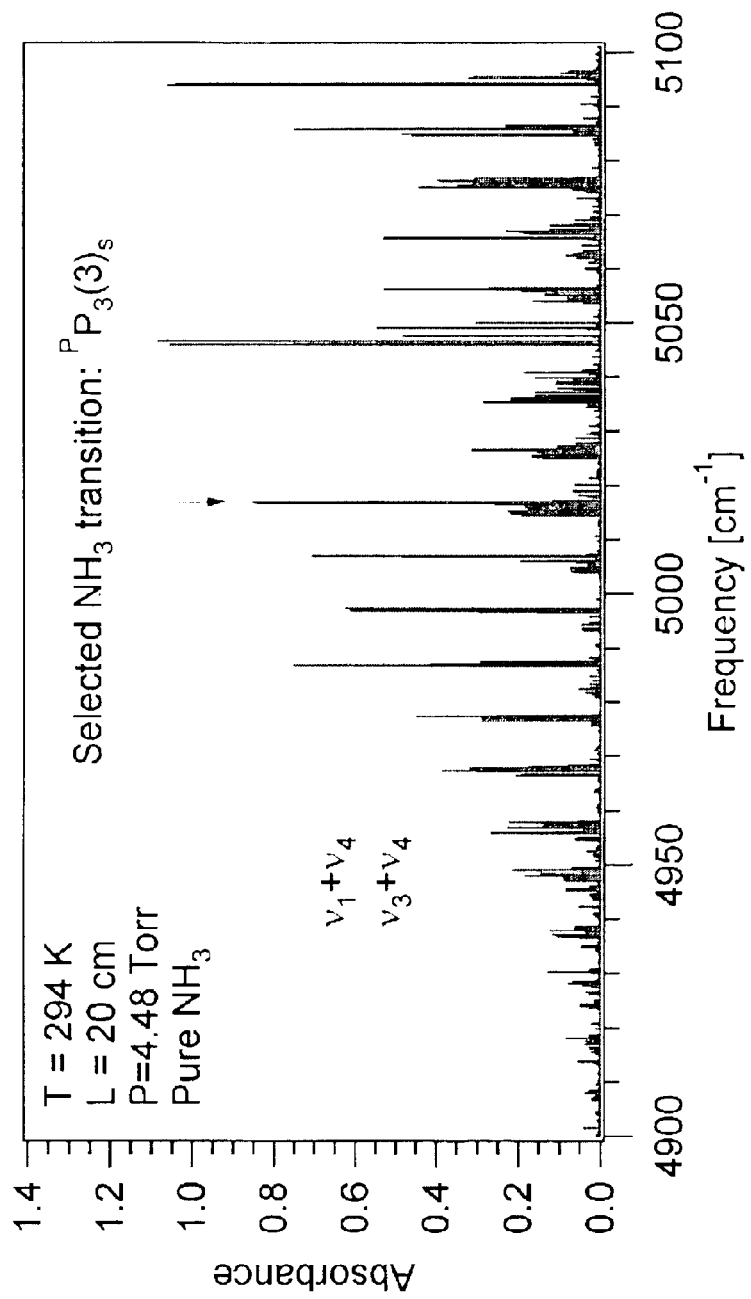
FIG. 2 shows measured survey spectra of pure $NH_3$ near 2.0 $\mu$m using an external cavity diode laser.
Figure 3:
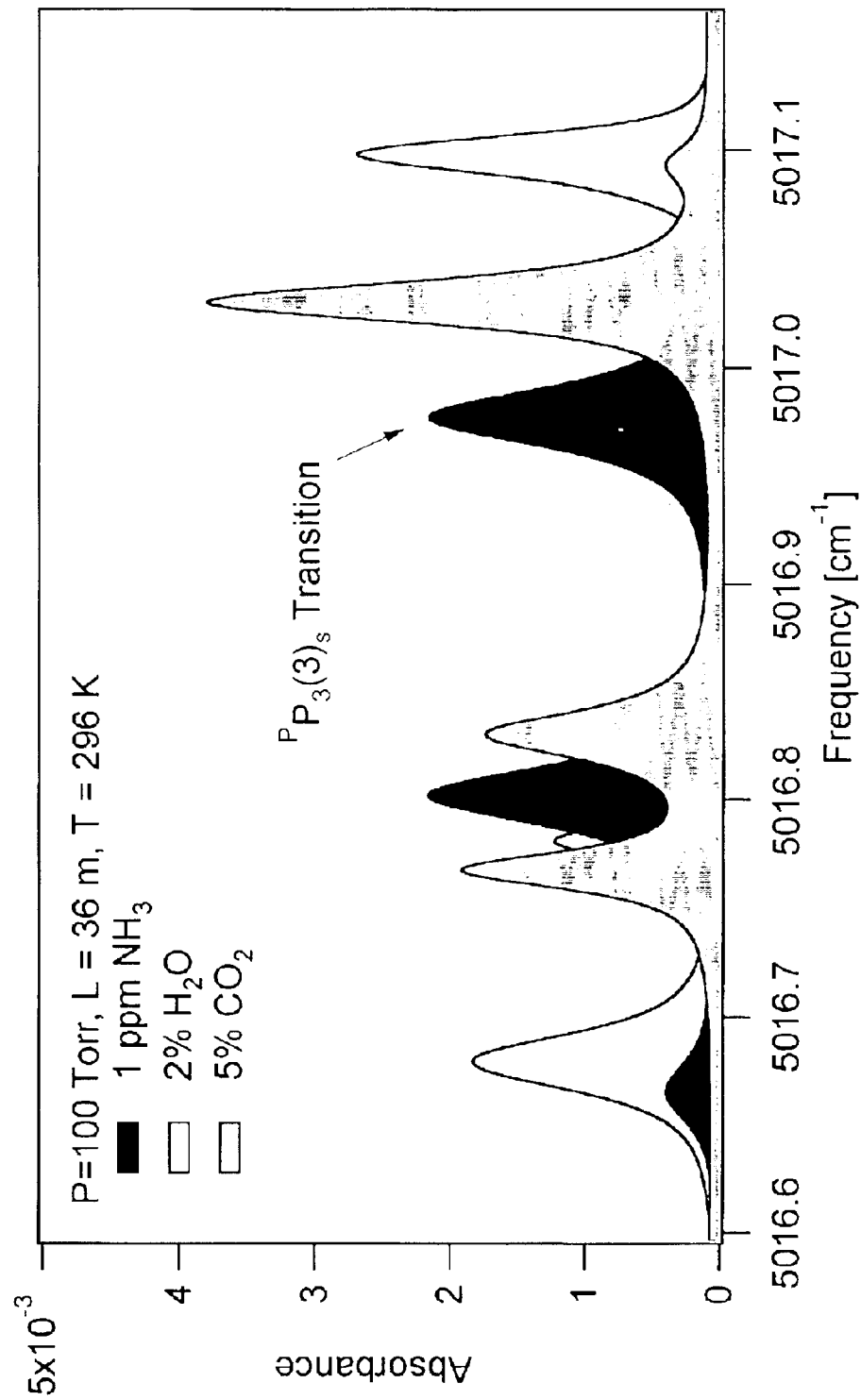
FIG. 3 shows calculated spectra near 5017 $cm^{-1}$ for 1 ppm $NH_3$, 5% $CO_2$, and 2% $H_2O$ with standard humidity.
Figure 4:
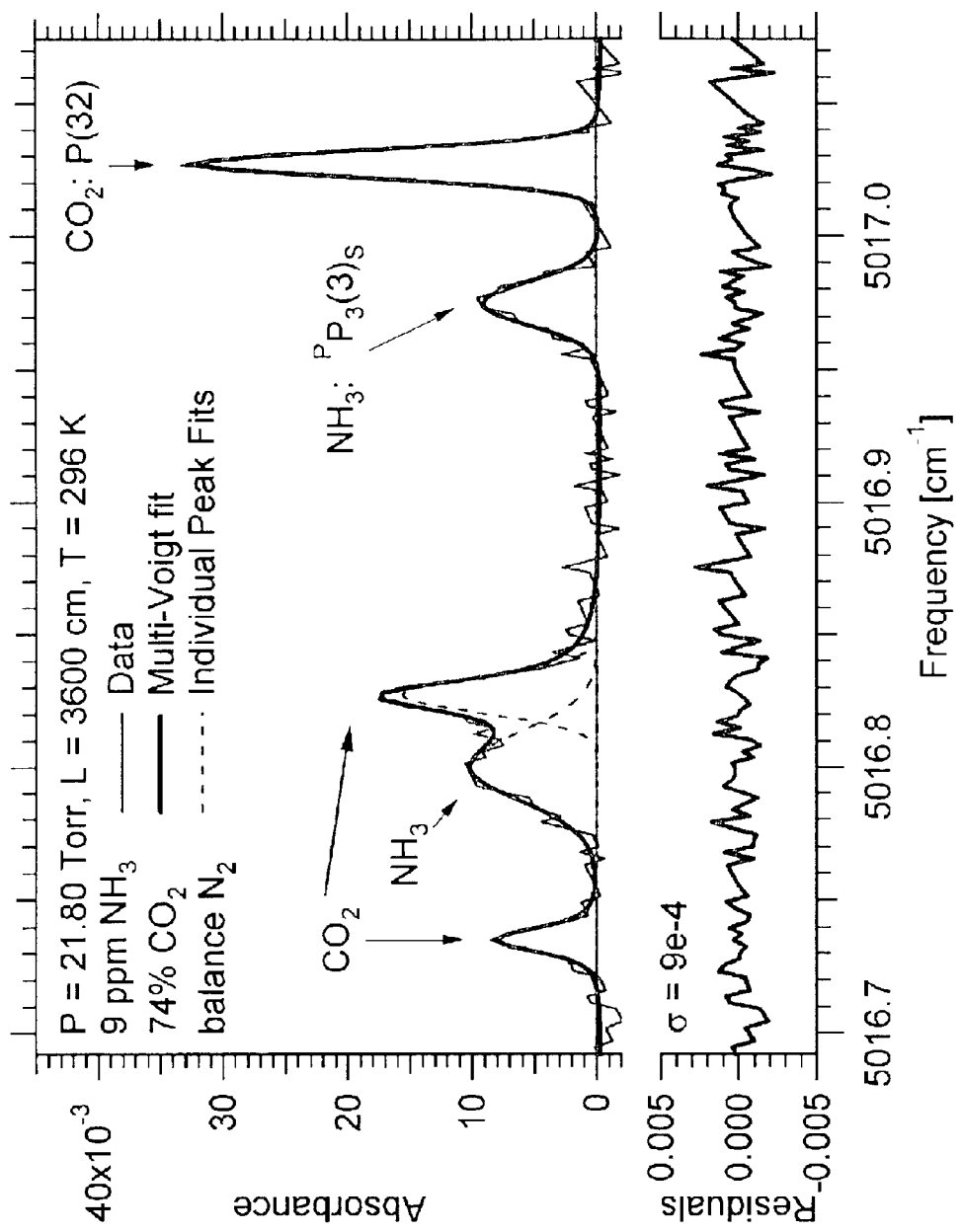
FIG. 4 shows measurements with a DFB diode laser confirming that the $NH_3$ transition at 5016.977 $cm^{-1}$ is isolated from interfering $H_2O$ and $CO_2$ absorption. The capacity to measure $NH_3$ and $CO_2$ simultaneously with a single laser sweep is also evident.

The line-strengths in the 2 µm region are approximately 100 times stronger for $CO_2$ as compared with the telecommunication wavelengths near 1.6 µm, and the $NH_3$ linestrengths at 2 µm are approximately three times stronger than at 1.5 µm. Sensitivity is directly dependent on absorption line strengths, thus the use of lasers at the longer wavelengths offers the opportunity for more sensitive detection. FIG. 2 shows the survey spectra of $NH_3$ recorded with an external-cavity diode laser from 4900 to 5100 $cm^{-1}$ (1960–2040 nm). The survey was used to qualitatively confirm the transition strengths and locations that are listed in the HITRAN96 database. The $CO_2$ bands near 2 µm were confirmed with previously published survey spectra (See paper by Mihalcea et al. (1998) entitled "*Diode laser absorption measurements of $CO_2$, $H_2O$, $N_2O$ and $NH_3$ near 2.0 micrometer*" and published in Appl. Phys. 67:283–288). Calculated spectra of $NH_3$, $CO_2$, and $H_2O$ were used to select optimum transitions for isolated species detection. The best choice for sensitive $NH_3$ monitoring in the presence of $CO_2$ and $H_2O$ is the $^P P_3(3)_s$ transition at 5016.977 $cm^{-1}$. This transition is part of a doublet that offers the third strongest absorption in the measured survey spectra at 2 µm, but as FIG. 3 depicts, is also isolated from $H_2O$ interference. The selected feature does have some overlap in the wings from the P(32) transition of $CO_2$ for large $CO_2$ concentrations, but that overlap is small enough such that quantitative measurements of ammonia concentration are still possible. Moreover, the proximity of the P(32) transition of $CO_2$ enables the advantageous opportunity for a single scan to yield measurements of both $NH_3$ and $CO_2$. Absorption from a flowing gas mixture of 9 ppm $NH_3$, 74% $CO_2$, and a balance of $N_2$ through a 3600 cm multipass cell was measured with a single sweep of the laser from 5016.7 to 5017.1 $cm^{-1}$ (see FIG. 4). The absorption spectra show five clear features, two from the $^P P_3(3)_s$ $NH_3$ doublet and three from neighboring $CO_2$ lines. These measurements confirm the following: (1) the $NH_3$ transition at 5016.802 $cm^{-1}$ suffers from significant $CO_2$ overlap, (2) the $NH_3$ transition at 5016.977 $cm^{-1}$ is sufficiently isolated from $CO_2$ interference at reduced pressures to yield quantitative measurements, and (3) a single scan can be used to measure trace $NH_3$ and major populations of $CO_2$ simultaneously.

Figure 5:
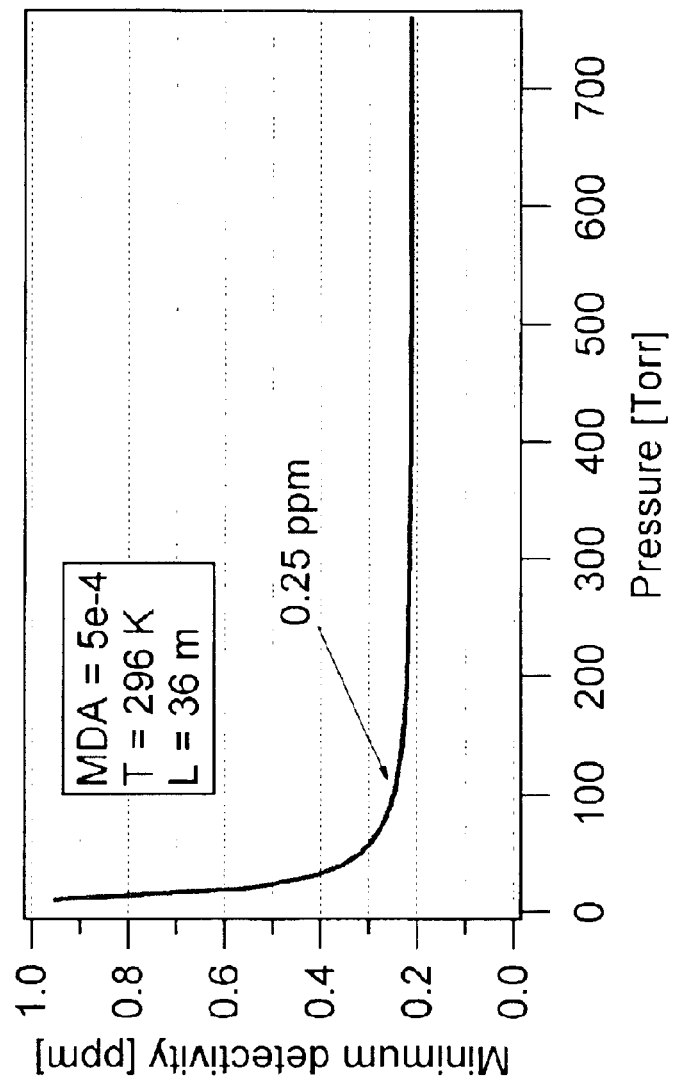
FIG. 5 shows predicted minimum mole fraction using peak absorption calculations for the $NH_3$ feature at 5016.977 $cm^{-1}$ for varying pressure conditions.

Using the measured line strengths (from Webber et al. (2001) in a paper entitled "*Measurements of $NH_3$ and $CO_2$ with distributed-feedback diode lasers near 2.0 µm in bioreactor vent gases*" and published in Appl. Opt. 40:4395–4403, which is hereby incorporated by reference), published lower-state energy, and published broadening coefficients, the minimum detectable mole fraction for the feature at 5016.977 $cm^{-1}$ for varying pressures at 296 K was predicted as shown in FIG. 5. As FIG. 5 reveals, 100 Torr is the optimum pressure for sensitive detection. At higher pressures the $NH_3$ population increases and the neighboring lines become blended, but the peak signal remains roughly the same, so higher pressures do not offer increased ability to distinguish absorption signals from background noise. At lower pressures, the population of $NH_3$ molecules decreases, giving less overall signal. The minimum detectivity at 100 Torr and 296 K is roughly 0.25 ppm for $NH_3$ at 5016.977 $cm^{-1}$, assuming a minimum detectable absorbance equal to $5 \times 10^{-4}$ and an optical pathlength of 36 m.

Figure 6:
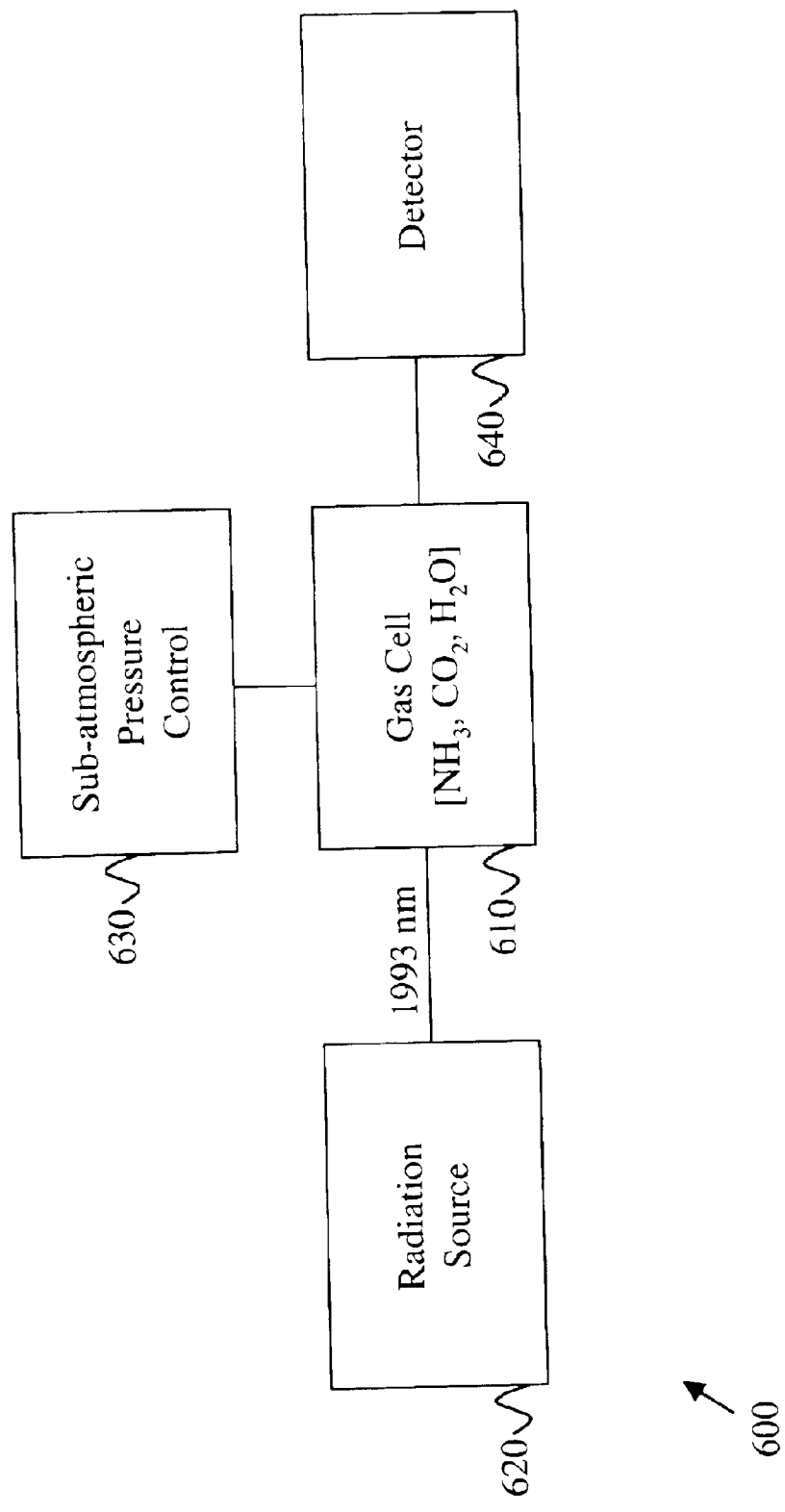
FIG. 6 shows an example of a measurement setup according to the present invention.

In summary, the present invention provides a system and method to measure the concentration of trace ammonia gas in the presence of large carbon dioxide and water vapor populations. For measuring ammonia only, a small scan by a radiation source would suffice. The present invention also provides a system and method to measure any combination of ammonia, carbon dioxide and water simultaneously with a radiation source (e.g. a tunable laser) that can sweep over the transitions from all species simultaneously. FIG. 6 shows an exemplary embodiment of a setup 600 according to the present system and method with a gas cell 610 containing at least $NH_3$, $CO_2$ and $H_2$. The preferred radiation source 620 to spectrally interrogate the gas species is an infra-red single-frequency laser. Furthermore, it would be preferred to have the radiation source operating at a wavelength substantially near 1993 nm. The infra-red single-frequency lasers that can be used are, for instance, but not limited to, a semiconductor diode laser, a distributed feedback diode laser, a fiber-coupled distributed feedback diode laser, a fiber laser, or an optical parametric oscillator. In order to spectrally resolve the measurements of the different gas species various different techniques could be used that are well known in the art to which this invention pertains, and would therefore include additional electronics for tasks such as sensor control, data acquisition and data analysis. For instance, the system and method of the present invention could utilize scanned- and fixed wavelength absorption, balanced radiometric detection, frequency modulated (FM) spectroscopy, cavity-ring down, stark modulation, evanescent wave, photothermal deflection, optogalvanic spectroscopy or photoacoustic spectroscopy. A means to operate at sub-atmospheric pressure 630 is included to yield a good balance between signal strength and isolation of neighboring spectral transitions. In a particular embodiment, means to operate at sub-atmospheric pressure 630 could for instance be a vacuum pump to maintain the pressure in gas cell 610 at substantially near 100 Torr (+/−20 Torr). A detector 640 is included to detect the appropriate signals (e.g. optical transmission for absorption spectroscopy, or acoustic power for photoacoustic spectroscopy) from gas cell 610 during the measurement. The detected data can then be further processed in a computer system or data analyzer.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, the present invention could be varied by including optical fibers for remote detection and measurement(s). The present invention could also be varied by providing optical fibers for remote detection or detection of multiple species and/or at multiple locations of the measurement(s). All such variations are considered to be within the scope and spirit of the present invention as defined by the following claims and their legal equivalents.

What is claimed is:

1. A sensor system for measuring ammonia in an environment containing carbon dioxide and water vapor, comprising a radiation source to spectrally interrogate the $^PP_3(3)_s$ ammonia transition which occurs at a frequency substantially close to 5016.977 inverse centimeters and which is substantially isolated from interfering absorption from said carbon dioxide and said water vapor.

2. The system as set forth in claim 1, further comprising said radiation source to spectrally interrogate a carbon dioxide transition in an absorption band at substantially near 2 $\mu$m, wherein said carbon dioxide transition is substantially isolated from interfering absorption from said ammonia and said water vapor.

3. The system as set forth in claim 2, wherein said carbon dioxide transition occurs at a frequency substantially close to 5017.030 inverse centimeters to avoid said interfering absorption from said ammonia and said water vapor.

4. The system as set forth in claim 1, further comprising said radiation source to spectrally interrogate a water vapor transition in an absorption band at substantially near 2 $\mu$m, wherein said water vapor transition is substantially isolated from interfering absorption from said ammonia and said carbon dioxide.

5. The system as set forth in claim 4, wherein said water vapor transition occurs at a frequency substantially close to 5017.100 inverse centimeters to avoid said interfering absorption from said ammonia and said carbon dioxide.

6. The system as set forth in claim 1, wherein said radiation source spectrally interrogates said ammonia transition, a carbon dioxide transition and a water vapor transition in an absorption band substantially near 2 $\mu$m and within a tunable range of said radiation source, wherein said ammonia transition, said carbon dioxide transition and said water vapor transition are substantially isolated from interfering absorption from each other.

7. The system as set forth in claim 1, further comprising means to operate at sub-atmospheric pressure to yield a good balance between signal strength and isolation of neighboring spectral transitions, wherein said sub-atmospheric pressure is substantially near 100 Torr for measurements of ammonia.

8. The system as set forth in claim 1, wherein said radiation source operates substantially near 1993 nm or substantially close to 5016.977 inverse centimeters.

9. The system as set forth in claim 1, wherein said radiation source is an infra-red single-frequency laser.

10. The system as set forth in claim 1, wherein said radiation source is a semiconductor diode laser.

11. The system as set forth in claim 1, wherein said radiation source comprises a distributed feedback diode laser, a fiber-coupled distributed feedback diode laser, a fiber laser, or an optical parametric oscillator.

12. The system as set forth in claim 1, wherein said interrogation utilizes a spectrally resolved technique, wherein said spectrally resolved technique comprises scanned- and fixed wavelength absorption, balanced radiometric detection, frequency modulated (FM) spectroscopy, cavity-ring down, stark modulation, evanescent wave, photothermal deflection, optogalvanic spectroscopy or photoacoustic spectroscopy.

13. The system as set forth in claim 1, further comprising optical fibers for remote detection.

14. The system as set forth in claim 1, further comprising optical fibers for remote detection, detection of multiple species or detection at multiple locations.

15. A method for measuring ammonia in an environment containing carbon dioxide and water vapor, comprising the steps of:
(a) providing a radiation source;
(b) operating said radiation source at a wavelength substantially near 2 $\mu$m; and
(c) utilizing said radiation source to spectrally interrogate the $^PP_3(3)_s$ ammonia transition in an absorption band at said wavelength substantially near 2 $\mu$m, wherein said ammonia transition is substantially isolated from interfering absorption from said carbon dioxide and said water vapor.

16. The method as set forth in claim 15, wherein said ammonia transition occurs at a frequency of substantially close to 5016.977 inverse centimeters to avoid said interfering absorption from said carbon dioxide and said water vapor.

17. The method as set forth in claim 15, further comprising said radiation source to spectrally interrogate a carbon dioxide transition in an absorption band at said wavelength substantially near 2 $\mu$m, wherein said carbon dioxide transition is substantially isolated from interfering absorption from said ammonia and said water vapor.

18. The method as set forth in claim 17, wherein said carbon dioxide transition is selected at a frequency of substantially close to 5017.030 inverse centimeters to avoid said interfering absorption from said ammonia and said water vapor.

19. The method as set forth in claim 15, further comprising said radiation source to spectrally interrogate a water vapor transition in an absorption band at said wavelength substantially near 2 $\mu$m, wherein said water vapor transition is substantially isolated from interfering absorption from said ammonia and said carbon dioxide.

20. The method as set forth in claim 19, wherein said water vapor transition is selected at a frequency of substantially close to 5017.100 inverse centimeters to avoid said interfering absorption from said ammonia and said carbon dioxide.

21. The method as set forth in claim 15, wherein said radiation source spectrally interrogates said ammonia transition, a carbon dioxide transition and a water vapor transition in an absorption band substantially near 2 $\mu$m and within a tunable range of said radiation source, wherein said ammonia transition, said carbon dioxide transition and said water vapor transition are substantially isolated from interfering absorption from each other.

22. The method as set forth in claim 15, further comprising means to operate at sub-atmospheric pressure substantially near 100 Torr to optimize signal and isolation from interfering absorption.

23. The method as set forth in claim 15, wherein said radiation source operates substantially near 1993 nm or substantially close to 5016.977 inverse centimeters.

24. The method as set forth in claim 15, wherein said radiation source is an infra-red single-frequency laser.

25. The method as set forth in claim 15, wherein said radiation source is a semiconductor diode laser.

26. The method as set forth in claim 15, wherein said radiation source comprises a distributed feedback diode laser, a fiber-coupled distributed feedback diode laser, a fiber laser, or an optical parametric oscillator.

27. The method as set forth in claim 15, wherein said interrogation utilizes a spectrally resolved technique, wherein said spectrally resolved technique comprises scanned- and fixed wavelength absorption, balanced radiometric detection, frequency modulated (FM) spectroscopy, cavity-ring down, stark modulation, evanescent wave, photothermal deflection, optogalvanic spectroscopy or photoacoustic spectroscopy.

28. The method as set forth in claim 15, further comprising the step of providing optical fibers for remote detection.

29. The method as set forth in claim 15, further comprising the step of providing optical fibers for remote detection, detection of multiple species or detection at multiple locations.

30. A sensor system having a single radiation source operating at a wavelength of substantially near 2 $\mu$m for simultaneously measuring a plurality of species along a single optical path in a gas mixture containing said plurality of species, including at least ammonia, carbon dioxide and water vapor, wherein the absorption transitions to be interrogated for said plurality of species are proximate in frequency such that the radiation source can be scanned or stepped in wavelength across the absorption transitions of said plurality of species within a single measurement cycle and wherein each one of said absorption transitions, including the $^PP_3(3)_s$ ammonia transition, a carbon dioxide transition, and a water vapor transition, is substantially isolated from interfering absorption of other species of said plurality of species.

31. The system as set forth in claim 30, further comprising one or more additional radiation sources each operating at said wavelength of substantially near 2 $\mu$m to spectrally interrogate said absorption transitions of one or more of said plurality of species, wherein said absorption transitions are substantially isolated from said interfering absorptions from said other species of said plurality of species.

32. The system as set forth in claim 30, wherein said ammonia transition is selected at a frequency of substantially close to 5016.977 inverse centimeters to avoid said interfering absorption from said carbon dioxide and said water vapor.

33. The system as set forth in claim 30, wherein said carbon dioxide transition occurs at a frequency of substantially close to 5017.030 inverse centimeters to avoid said interfering absorption from said ammonia and said water vapor.

34. The system as set forth in claim 30, wherein said water vapor transition occurs at a frequency of substantially close to 5017.100 inverse centimeters to avoid said interfering absorption from said ammonia and said carbon dioxide.

35. The system as set forth in claim 30, further comprising means to operate at sub-atmospheric pressure, wherein said sub-atmospheric is substantially near 100 Torr.

36. The system as set forth in claim 30, wherein said radiation source operates substantially near 1993 nm or substantially close to 5016.977 inverse centimeters.

37. The system as set forth in claim 30, wherein said radiation source is an infra-red single-frequency laser.

38. The system as set forth in claim 30, wherein said radiation source is a semiconductor diode laser.

39. The system as set forth in claim 30, wherein said radiation source comprises a distributed feedback diode laser, a fiber-coupled distributed feedback diode laser, a fiber laser, or an optical parametric oscillator.

40. The system as set forth in claim 30, wherein said interrogation utilizes a spectrally resolved technique, wherein said spectrally resolved technique comprises scanned- and fixed wavelength absorption, balanced radiometric detection, frequency modulated (FM) spectroscopy, cavity-ring down, stark modulation, evanescent wave, photothermal deflection, optogalvanic spectroscopy or photoacoustic spectroscopy.

41. The system as set forth in claim 30, further comprising optical fibers for remote detection.

42. The system as set forth in claim 30, further comprising optical fibers for remote detection, detection of multiple species or detection at multiple locations.

43. A method for simultaneously measuring with a single radiation source operating at a wavelength of substantially near 2 µm a plurality of species along a single optical path in a gas mixture containing said plurality of species, including at least ammonia, carbon dioxide and water vapor, wherein the absorption transitions to be interrogated for said plurality of species are proximate in frequency such that the radiation source can be scanned or stepped in said wavelength across the absorption transitions of said plurality of species within a single measurement cycle and wherein each one of said absorption transitions, including the ${}^{P}P_3(3)_s$ ammonia transition, a carbon dioxide transition, and a water vapor transition, is substantially isolated from interfering absorption of other species of said plurality of species.

44. The method as set forth in claim 43, further comprising the step of providing one or more additional radiation sources each operating at said wavelength of substantially near 2 µm to spectrally interrogate said absorption transitions of one or more of said plurality of species, wherein said absorption transitions are substantially isolated from said interfering absorptions from said other species of said plurality of species.

45. The method as set forth in claim 43, wherein said ammonia transition is selected at a frequency of substantially close to 5016.977 inverse centimeters to avoid said interfering absorption from said carbon dioxide and said water vapor.

46. The method as set forth in claim 43, wherein said carbon dioxide transition occurs at a frequency of substantially close to 5017.030 inverse centimeters to avoid said interfering absorption from said ammonia and said water vapor.

47. The method as set forth in claim 43, wherein said water vapor transition occurs at a frequency of substantially close to 5017.100 inverse centimeters to avoid said interfering absorption from said ammonia and said carbon dioxide.

48. The method as set forth in claim 43, further comprising means to operate at sub-atmospheric pressure, wherein said sub-atmospheric pressure is substantially near 100 Torr.

49. The method as set forth in claim 43, wherein said radiation source operates substantially near 1993 nm or substantially close to 5016.977 inverse centimeters.

50. The method as set forth in claim 43, wherein said radiation source is an infra-red single-frequency laser.

51. The method as set forth in claim 43, wherein said radiation source is a semiconductor diode laser.

52. The method as set forth in claim 43, wherein said radiation source comprises a distributed feedback diode laser, a fiber-coupled distributed feedback diode laser, a fiber laser, or an optical parametric oscillator.

53. The method as set forth in claim 43, wherein said interrogation utilizes a spectrally resolved technique, wherein said spectrally resolved technique comprises scanned- and fixed wavelength absorption, balanced radiometric detection, frequency modulated (FM) spectroscopy, cavity-ring down, stark modulation, evanescent wave, photothermal deflection, optogalvanic spectroscopy or photoacoustic spectroscopy.

54. The method as set forth in claim 43, further comprising the step of providing optical fibers for remote detection.

55. The method as set forth in claim 43, further comprising the step of providing optical fibers for remote detection, detection of multiple species or detection at multiple locations.

* * * * *